(12) United States Patent
Lee et al.

(10) Patent No.: US 11,419,527 B2
(45) Date of Patent: Aug. 23, 2022

(54) APPARATUS AND METHOD FOR ESTIMATING BLOOD CONCENTRATION OF ANALYTE, AND APPARATUS AND METHOD FOR GENERATING MODEL

(71) Applicant: SAMSUNG ELECTRONICS CO., LTD., Suwon-si (KR)

(72) Inventors: Joon Hyung Lee, Seongnam-si (KR); Won Jong Jung, Seoul (KR); Kak Namkoong, Seoul (KR); Jung Yong Nam, Hwaseong-si (KR); Yeol Ho Lee, Anyang-si (KR); Ki Young Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 184 days.

(21) Appl. No.: 16/591,006

(22) Filed: Oct. 2, 2019

(65) Prior Publication Data
US 2020/0100710 A1    Apr. 2, 2020

(30) Foreign Application Priority Data
Oct. 2, 2018    (KR) ........................ 10-2018-0117375

(51) Int. Cl.
*A61B 5/1455*    (2006.01)
*A61B 5/145*    (2006.01)
(Continued)

(52) U.S. Cl.
CPC ........ *A61B 5/1455* (2013.01); *A61B 5/14532* (2013.01); *A61B 5/14546* (2013.01);
(Continued)

(58) Field of Classification Search
CPC ... A61B 5/14532; A61B 5/14546; A61B 5/72; A61B 5/7264; A61B 5/7275;
(Continued)

(56) References Cited

U.S. PATENT DOCUMENTS

| 5,957,841 A | 9/1999 | Maruo et al. |
| 6,280,381 B1 | 8/2001 | Malin et al. |

(Continued)

FOREIGN PATENT DOCUMENTS

| EP | 1452135 A1 * | 9/2004 | ......... A61B 5/14532 |
| GB | 2489717 A * | 10/2012 | ............ G01J 3/0262 |

(Continued)

OTHER PUBLICATIONS

Lloyd J. Edwards et al., "A method for fitting regression splines with varying polynomial order in the linear mixed model", Sep. 12, 2005, Wiley Inter Science, Statistics in Medicine DOI: 10.1002/sim.2232, pp. 513-527, (15 pages total).

(Continued)

*Primary Examiner* — Eric F Winakur
*Assistant Examiner* — Alice Ling Zou
(74) *Attorney, Agent, or Firm* — Sughrue Mion, PLLC

(57) ABSTRACT

An apparatus for estimating blood concentration may include an optical sensor configured to emit light towards a skin surface of a user, and detect an optical signal reflected by the skin surface of the user, and a processor configured to select an interval-specific blood concentration estimation model, from among a plurality of interval-specific blood concentration estimation models, based on an interval selection indicator and estimate a blood concentration change or a blood concentration of an analyte using the selected interval-specific blood concentration estimation model and the detected optical signal.

17 Claims, 9 Drawing Sheets

(51) Int. Cl.
*A61B 5/00* (2006.01)
*G05B 17/02* (2006.01)

(52) U.S. Cl.
CPC ............ *G05B 17/02* (2013.01); *A61B 5/7264* (2013.01); *A61B 2562/0238* (2013.01)

(58) Field of Classification Search
CPC ... A61B 5/7271; A61B 5/1455; A61B 5/0075; A61B 5/1495; A61B 5/7267; A61B 5/7278
See application file for complete search history.

(56) References Cited

U.S. PATENT DOCUMENTS

| | | |
|---|---|---|
| 7,308,366 B2 | 12/2007 | Han |
| 2002/0016535 A1* | 2/2002 | Martin ................ A61B 5/0031 600/319 |
| 2005/0187445 A1 | 8/2005 | Han |
| 2006/0167350 A1 | 7/2006 | Monfre et al. |
| 2007/0179367 A1 | 8/2007 | Ruchti et al. |
| 2012/0283530 A1 | 11/2012 | Maynard et al. |
| 2016/0026770 A1 | 1/2016 | Tanaka et al. |
| 2018/0146899 A1 | 5/2018 | Lee et al. |
| 2018/0183541 A9 | 6/2018 | Zocchi et al. |

FOREIGN PATENT DOCUMENTS

| | | | |
|---|---|---|---|
| KR | 10-0682888 B1 | 2/2007 | |
| KR | 10-2012-0130164 A | 11/2012 | |
| KR | 10-2015-0140363 A | 12/2015 | |
| KR | 10-1807809 B1 | 12/2017 | |
| WO | WO-0210725 A2 * | 2/2002 | ........... A61B 5/1455 |
| WO | 2007/064796 A2 | 6/2007 | |

OTHER PUBLICATIONS

G Bedogni et al., "Accuracy of an eight-point tactile-electrode impedance method in the assessment of total body water", European Journal of Clinical Nutrition, 2002, pp. 1143-1148, (6 pages total).

Angelica Aviles, "Cardiovascular risk factors among Ecuadorian adolescents: a school-based health promotion intervention", 2015, Doctoral thesis, Ghent University, pp. 1-172, (194 pages total).

Communication dated Dec. 11, 2019, issued by the European Patent Office in counterpart European Application No. 19201061.9.

* cited by examiner

APPARATUS AND METHOD FOR ESTIMATING BLOOD CONCENTRATION OF ANALYTE, AND APPARATUS AND METHOD FOR GENERATING MODEL

CROSS-REFERENCE TO RELATED APPLICATION(S)

This application is based on and claims priority under 35 U.S.C. § 119 to Korean Patent Application No. 10-2018-0117375, filed on Oct. 2, 2018, in the Korean Intellectual Property Office, the disclosure of which is incorporated by reference herein in its entirety.

BACKGROUND

1. Field

The disclosure relates to noninvasive measurement of blood concentration of an analyte.

2. Description of Related Art

A level of triglycerides in blood is elevated in a 6 to 7 hour period due to fat intake and then is decreased. Thus, measuring an amount of triglyceride change due to fat intake may be an important health indicator, such as an amount of fat intake, fat-decomposition ability, and the like, from the viewpoint of healthcare objectives.

As one of the methods for measuring triglyceride, there is an invasive method of collecting and analyzing blood at intervals of 15 to 20 minutes. The invasive method of measuring a blood triglyceride level has high reliability of measurement, but the use of injection may cause pain during blood sampling, inconvenience, and a risk of infection. Recently, a noninvasive method of measuring an amount of triglyceride change by measuring an optical property, without directly collecting blood, has been studied.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The disclosure relates to an apparatus and method for estimating blood concentration of an analyte and an apparatus and method for generating a model therefor.

In accordance with an aspect of the disclosure, there is provided an apparatus for estimating blood concentration including an optical sensor configured to emit light towards a skin surface of a user, and detect an optical signal reflected by the skin surface of the user, and a processor configured to select an interval-specific blood concentration estimation model, from among a plurality of interval-specific blood concentration estimation models, based on an interval selection indicator and estimate a blood concentration change or a blood concentration of an analyte using the selected interval-specific blood concentration estimation model and the detected optical signal.

The processor may obtain a plurality of interval selection factors, and determine the interval selection indicator by linearly or nonlinearly combining the obtained plurality of interval selection factors.

The plurality of selection interval factors may include at least one of an initial value of an optical property, a height, a weight, a body mass index (BMI), and a body fat.

The processor may select a blood concentration change interval based on the interval selection indicator, and may select the interval-specific blood concentration estimation model that corresponds to the selected blood concentration change interval from among the plurality of interval-specific blood concentration estimation models.

The processor may determine a change of an optical property based on the detected optical signal, and estimate the blood concentration change or blood concentration of the analyte using the determined change of the optical property and the selected interval-specific blood concentration estimation model.

The optical property may be a scattering coefficient or an effective attenuation coefficient.

The analyte may include at least one of glucose, triglyceride, cholesterol, protein, lactate, ethanol, uric acid, and ascorbic acid.

The plurality of interval-specific blood concentration estimation models may be generated based on training data classified based on an interval division indicator that corresponds to the interval selection indicator.

The apparatus may further include an output interface configured to output the estimated blood concentration change or the blood concentration of the analyte.

In accordance with an aspect of the disclosure, there is provided a method of estimating blood concentration including emitting light towards a skin surface of a user, detecting an optical signal reflected by the skin surface of the user, selecting an interval-specific blood concentration estimation model, from among a plurality of interval-specific blood concentration estimation models, based on an interval selection indicator, and estimating a blood concentration change or a blood concentration of an analyte using the selected interval-specific blood concentration estimation model and the detected optical signal.

The method may further include obtaining a plurality of interval selection factors, and determining the interval selection indicator by linearly or nonlinearly combining the obtained plurality of interval selection factors.

The plurality of selection interval factors may include at least one of an initial value of an optical property, a height, a weight, a body mass index (BMI), and a body fat.

The selecting the interval-specific blood concentration estimation model may include selecting a blood concentration change interval based on the interval selection indicator, and selecting the interval-specific blood concentration estimation model that corresponds to the selected blood concentration change interval from among the plurality of interval-specific blood concentration estimation models.

The estimating of the blood concentration change or the blood concentration of the analyte may include determining a change of an optical property based on the detected optical signal, and estimating the blood concentration change or the blood concentration of the analyte using the determined change of the optical property and the selected interval-specific blood concentration estimation model.

The optical property may be a scattering coefficient or an effective attenuation coefficient.

The analyte may include at least one of glucose, triglyceride, cholesterol, protein, lactate, ethanol, uric acid, and ascorbic acid.

The plurality of interval-specific blood concentration estimation models are generated based on training data classified according to an interval division indicator that corresponds to the interval selection indicator.

The method may further include outputting the estimated blood concentration change or the blood concentration of the analyte.

In accordance with an aspect of the disclosure, there is provided an apparatus for generating a model including a processor configured to obtain, as training data, optical property change data, and blood concentration change data of an analyte that corresponds to the optical property change data, divide a blood concentration change of the analyte into a plurality of intervals based on an interval division indicator, classify the obtained training data for each interval of the plurality of intervals, and generate interval-specific blood concentration estimation models using the training data classified for each interval.

The interval division indicator may be formed by a linear or nonlinear combination of a plurality of interval division factors.

The plurality of interval division factors include at least one of an initial value of an optical property, a height, a weight, a body mass index (BMI), and a body fat.

The analyte may include at least one of glucose, triglyceride, cholesterol, protein, lactate, ethanol, uric acid, and ascorbic acid.

In accordance with an aspect of the disclosure, there is provided a method of generating a model including obtaining, as training data, optical property change data, and blood concentration change data of an analyte that corresponds to the optical property change data, dividing a blood concentration change of the analyte into a plurality of intervals based on an interval division indicator, classifying the obtained training data for each interval of the plurality of intervals, and generating interval-specific blood concentration estimation models using the training data classified for each interval.

The interval division indicator may be formed by a linear or nonlinear combination of a plurality of interval division factors.

The plurality of interval division factors may include at least one of an initial value of an optical property, a height, a weight, a body mass index (BMI), and a body fat.

The analyte may include at least one of glucose, triglyceride, cholesterol, protein, lactate, ethanol, uric acid, and ascorbic acid.

Other features and aspects will be apparent from the following detailed description, the drawings, and the claims.

BRIEF DESCRIPTION OF THE DRAWINGS

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Figure 1:
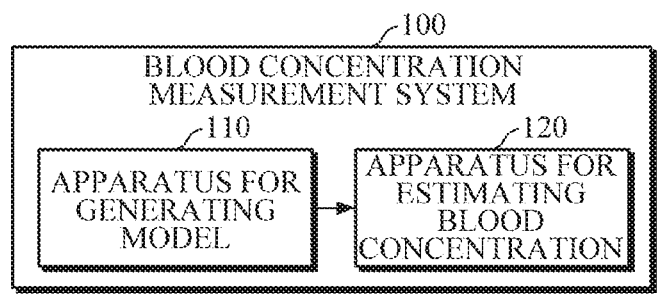
FIG. 1 is a block diagram illustrating a system for measuring blood concentration according to an embodiment.

The following detailed description is provided to assist the reader in gaining a comprehensive understanding of the methods, apparatuses, and/or systems described herein. Various changes, modifications, and equivalents of the systems, apparatuses and/or methods described herein should be apparent to those of ordinary skill in the art. In the following description, a detailed description of known functions and configurations incorporated herein may be omitted so as to not obscure the subject matter of the present disclosure. Throughout the drawings and the detailed description, unless otherwise described, the same drawing reference numerals may refer to the same elements, features, and structures. The relative size and depiction of these elements may be exaggerated for clarity, illustration, and convenience.

It should be noted that in some alternative implementations, the functions/acts noted in the blocks may occur in a different order than as shown in the flowcharts. For example, two blocks shown in succession may be executed substantially concurrently, may be executed in the reverse order, or may be executed in a non-successive manner depending upon the functionality/acts involved.

Terms described herein may be selected by considering functions in the embodiments and meanings may vary depending on, for example, a user or operator's intentions or customs. Therefore, in the following embodiments, when terms are specifically defined, the meanings of the terms may be interpreted based on the definitions, and otherwise, may be interpreted based on meanings recognized by those skilled in the art.

It should be understood that, although the terms "first," "second," etc. may be used herein to describe various elements, these elements might not be limited by these terms. These terms may be used to distinguish one element from another. Also, the singular forms may include the plural forms as well, unless the context clearly indicates otherwise. In the specification, unless explicitly described to the contrary, the word "comprise" and variations thereof such as "comprises" or "comprising" may be understood to imply the inclusion of stated elements but not the exclusion of any other elements. Terms such as "unit" and "module" may denote units that process at least one function or operation, and that may be implemented in hardware, software, or a combination of hardware and software.

FIG. 1 is a block diagram illustrating a system for measuring blood concentration according to an embodiment.

Referring to FIG. 1, the system 100 for measuring blood concentration may include an apparatus 110 for generating a model and an apparatus 120 for estimating blood concentration.

The apparatus 110 for generating a model may divide a blood concentration change or a normalized blood concentration change of an analyte into a plurality of intervals according to a predetermined interval division indicator, and generate a blood concentration estimation model for each interval. In this case, the analyte may include glucose, triglyceride, cholesterol, protein, lactate, ethanol, uric acid, ascorbic acid, and the like. The interval division indicator may be an indicator for dividing the blood concentration change or a normalized blood concentration change into a plurality of intervals, and may be formed by a linear or nonlinear combination of one or more interval division factors. The interval division factor may include a physiological characteristic, a physical characteristic, or an optical characteristic, such as an initial value of an optical property (e.g., scattering coefficient or effective attenuation coefficient), a height, a weight, a body mass index (BMI), a body fat, or the like.

The apparatus 120 for estimating blood concentration may select one of the blood concentration estimation models generated for each interval according to an interval selection indicator, and estimate blood concentration change or blood concentration of the analyte based on the selected blood concentration estimation model. In this case, the interval selection indicator may be an indicator to be used to select a model to be used for estimating blood concentration of the analyte, and may correspond to the interval division indicator. That is, the interval selection indicator may be determined by a linear or nonlinear combination of interval selection factors including a physiological characteristic, a physical characteristic, or an optical characteristic, such as an initial value of an optical property (e.g., scattering coefficient or effective attenuation coefficient), a height, a weight, a BMI, a body fat, or the like.

Figure 2:
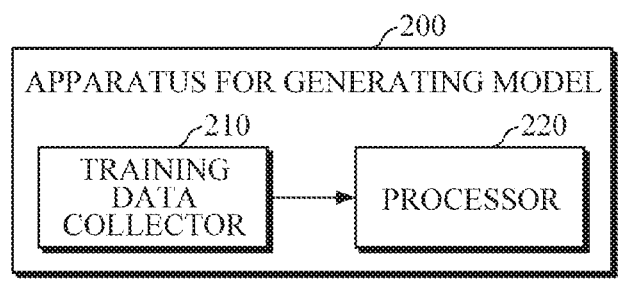
FIG. 2 is a block diagram illustrating an apparatus for generating a model according to an embodiment.

FIG. 2 is a block diagram illustrating an apparatus for generating a model according to an embodiment. The apparatus 200 for generating a model illustrated in FIG. 2 may be an embodiment of the apparatus 110 for generating a model shown in FIG. 1. The apparatus 200 for generating a model may be an apparatus which classifies a blood concentration change of an analyte into a plurality of intervals, and generates a blood concentration estimation model for each interval and may be mounted in an electronic device. The electronic device may include a mobile phone, a smartphone, a tablet computer, a notebook computer, a personal digital assistant (PDA), a portable multimedia player (PMP), a navigation system, an MP3 player, a digital camera, a wearable device, and the like. The wearable device may include a wrist watch type, a wrist band type, a ring type, a belt type, a necklace type, an ankle band type, a thigh band type, a forearm band type, and the like. However, the electronic device and the wearable device are not limited to the above-described examples.

Referring to FIG. 2, the apparatus 200 for generating a model may include a training data collector 210 and a processor 220.

The training data collector 210 may collect, as training data, optical property change data and blood concentration change data of an analyte that corresponds to the optical property change data. Alternatively, the training data collector 210 may collect, as training data, normalized optical property change data and normalized blood concentration change data of an analyte that corresponds to the normalized optical property change data. In this case, the normalized optical property change data may be data in which the optical property change data is normalized to an optical property initial value, and the normalized blood concentration change data may be data in which the blood concentration change data is normalized to a blood concentration initial value.

The processor 220 may divide the blood concentration change or the normalized blood concentration change of the analyte according to an interval division indicator and classify collected training data for each interval. As described above, the interval division indicator may be formed by a linear or nonlinear combination of interval division factors including an initial value of an optical property (e.g., scattering coefficient or effective attenuation coefficient), a height, a weight, a BMI, a body fat, and the like. For example, the interval division indicator may be represented as a linear combination of interval division factors as shown in Equation 1. However, this is merely an embodiment and the interval division indicator is not limited thereto.

$$y = \sum_i a_i \times x_i \qquad \text{Equation (1)}$$

Here, x denotes an interval division factor, $a_i$ denotes a weight to be applied to each interval division factor, and y denotes an interval division indicator.

For example, assuming that the blood concentration change or the normalized blood concentration change is divided into two intervals, the processor 220 may determine that an interval in which the interval division indicator y is less than or equal to a predetermined value is a first interval, and that an interval in which the interval division indicator y is greater than the predetermined value is a second interval. In addition, the processor 220 may classify the collected training data into training data of the first interval and training data of the second interval based on the interval division indicator y.

The processor 220 may generate a blood concentration estimation model for each interval by using the training data classified for each interval. In this case, the processor 220 may generate a blood concentration estimation model for each interval using a regression analysis technique, a machine learning, and the like. The regression analysis technique may include simple linear regression, multi-linear regression, logistic regression, proportional Cox regression, and the like, and the machine learning technique may include an artificial neural network, a decision tree, a genetic algorithm, genetic programming, K-nearest neighbor, a radial basis function network, random forest, support vector machine, deep-learning, and the like.

Figure 3:
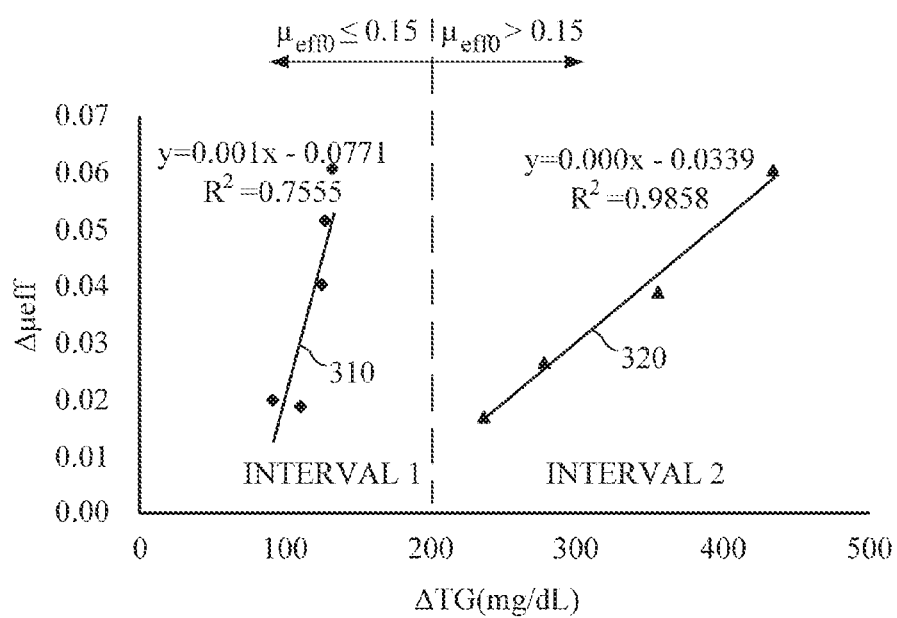
FIG. 3 is a diagram illustrating an example of a blood concentration estimation model generated for each blood concentration change interval according to an embodiment.

FIG. 3 is a diagram illustrating an example of a blood concentration estimation model generated for each blood concentration change interval according to an embodiment. FIG. 3 illustrates an example in which a blood concentration change of triglyceride is divided into two intervals based on an initial value of an effective attenuation coefficient.

Referring to FIGS. 2 and 3, the processor 220 may divide a blood concentration change interval ∇TG of trigrycelide into two intervals based on an initial value $\mu_{eff0}$ of an effective attenuation coefficient. In the illustrated example, the processor 220 may divide the blood concentration change interval ∇TG into an interval (interval 1) in which the initial value $\mu_{eff0}$ of the effective attenuation coefficient is less than or equal to 0.15, and an interval (interval 2) in which the initial value of the effective attenuation coefficient is greater than 0.15. In this case, as shown in FIG. 3, the blood concentration change interval ∇TG may be divided, based on 200 mg/dL, into an interval (interval 1) in which an amount of the blood concentration change is less than or equal to 200 mg/dL, and an interval (interval 2) in which an amount of blood concentration change is greater than 200 mg/dL.

The processor 220 may classify the collected training data training data in which the initial value $\mu_{eff0}$ of the effective attenuation coefficient is less than or equal to 0.15 as training data of the interval 1, and classify training data in which the initial value $\mu_{eff0}$ of the effective attenuation coefficient is greater than 0.15 as training data of the interval 2. In addition, the processor 220 may generate a blood concentration estimation model 310 of the interval 1 using the training data of the interval 1, and generate a blood concentration estimation model 320 of the interval 2 using the training data of the interval 2.

Figure 4:
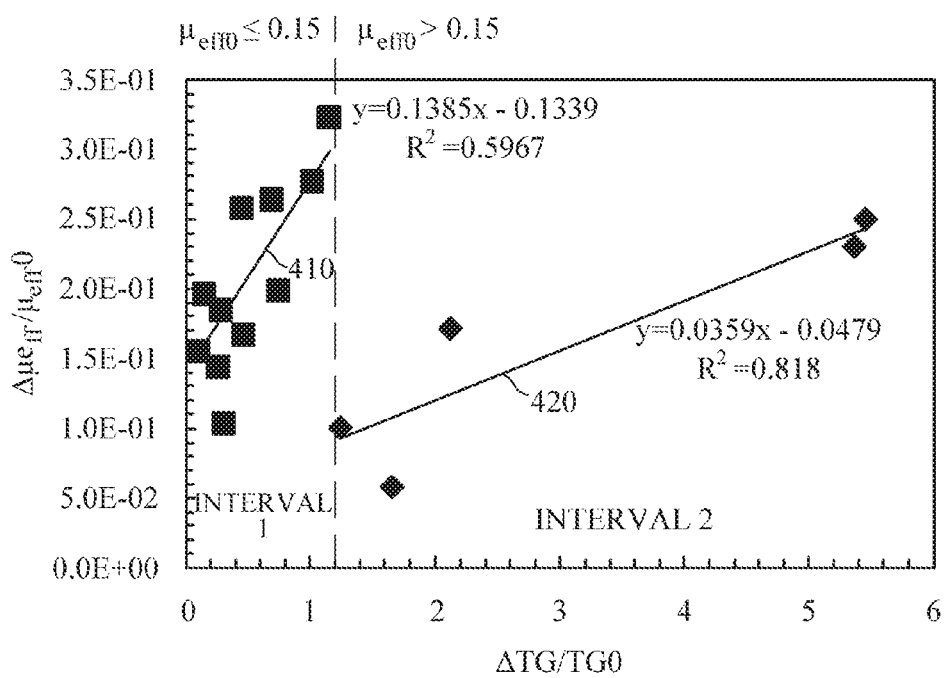
FIG. 4 is a diagram illustrating an example of a blood concentration estimation model generated for each of a plurality of normalized blood concentration change intervals according to an embodiment.

FIG. 4 is a diagram illustrating an example of a blood concentration estimation model generated for each of a plurality of normalized blood concentration change intervals according to an embodiment. FIG. 4 illustrates that a normalized blood concentration change interval of triglyceride into two intervals based on an initial value of an effective attenuation coefficient.

Referring to FIGS. 2 and 4, the processor 220 may divide a blood concentration change interval $\nabla TG/TG0$ normalized to an initial blood concentration value into two intervals based on an initial value $\mu_{eff0}$ of an effective attenuation coefficient. In the illustrated example, the processor 220 may divide the normalized blood concentration change interval into an interval (interval 1) in which the initial value $\mu_{eff0}$ of the effective attenuation coefficient is less than or equal to 0.15, and an interval (interval 2) in which the initial value $\mu_{eff0}$ of the effective attenuation coefficient is greater than 0.15. In this case, as shown in FIG. 4, the blood concentration change interval $\nabla TG/TG0$ normalized to an initial blood concentration value may be divided, based on 1.2, into an interval (interval 1) in which a value of $\nabla TG/TG0$ is less than or equal to 1.2 and an interval (interval 2) in which a value of $\nabla TG/TG0$ is greater than 1.2.

The processor 220 may classify, among the collected training data, training data in which the initial value of the effective attenuation coefficients $\mu_{eff0}$ is less than or equal to 0.15 as training data of the interval 1, and classify training data in which the initial value of the effective attenuation coefficient $\mu_{eff0}$ is greater than 0.15 as training date of the interval 2. In addition, the processor 220 may generate a blood concentration estimation model 410 of the interval 1 by using the training data of the interval 1, and may generate a blood concentration estimation model 420 by using the training data of the interval 2.

Figure 5:
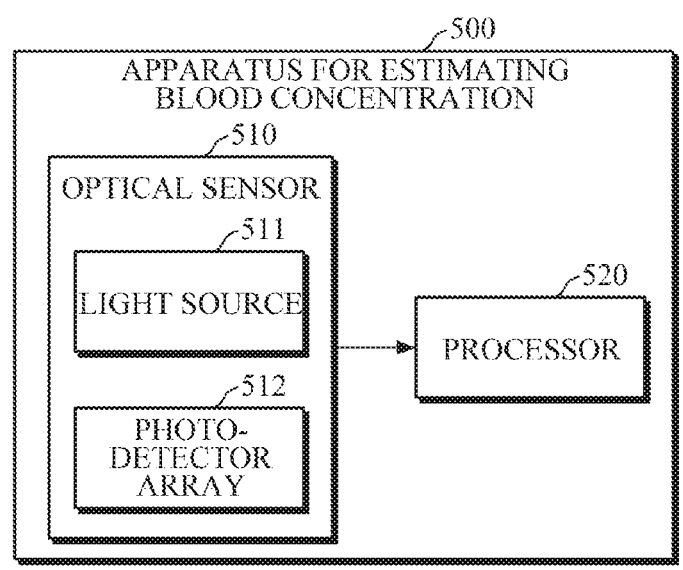
FIG. 5 is a block diagram illustrating an apparatus for estimating blood concentration according to an embodiment.

FIG. 5 is a block diagram illustrating an apparatus for estimating blood concentration according to an embodiment. The apparatus 500 for estimating blood concentration of FIG. 5 may be an embodiment of the apparatus 120 for estimating blood concentration shown in FIG. 1. The apparatus 500 for estimating blood concentration may be an apparatus configured to measure blood concentration or blood concentration change of an analyte in a noninvasive manner using an optical signal, and may be mounted in an electronic device. The electronic device may include a mobile phone, a smartphone, a tablet computer, a notebook computer, a PDA, a PMP, a navigation system, an MP3 player, a digital camera, a wearable device, and the like. The wearable device may include a wrist watch type, a wrist band type, a ring type, a belt type, a necklace type, an ankle band type, a thigh band type, a forearm band type, and the like. However, the electronic device and the wearable device are not limited to the above-described examples.

Referring to FIG. 5, the apparatus 500 for estimating blood concentration may include an optical sensor 510 and a processor 520.

The optical sensor 510 may emit light towards the user's skin and detect an optical signal reflected by the skin. The optical sensor 510 may include a light source 511 and a photodetector array 512.

The light source 511 may emit light towards an object. For example, the light source 511 may emit light of a predetermined wavelength, for example, near-infrared (NIR) light, towards the object. However, a wavelength of light emitted from the light source 511 may vary according to the purpose of measurement or the type of the analyte. In addition, the light source 511 may be formed as a single light emitter, or may be formed as a plurality of light emitters. In the case where the light source 511 is formed as a plurality of light emitters, the group of light emitters may emit light having different wavelengths from each other or may emit light having the same wavelength. According to an embodiment, the light source 511 may include a light emitting diode (LED), a laser diode, a phosphor, and the like, but these are merely examples, and the light source 511 is not limited thereto.

The photodetector array 512 may include a plurality of photodetectors. Each of the photodetectors may detect an optical signal reflected by the skin, and measure intensity of the detected optical signal. According to an embodiment, each of the photodetectors may include a photodiode, a phototransistor, or a charge-coupled device (CCD), but is not limited thereto.

The processor 520 may control an overall operation of the apparatus 500 for estimating blood concentration.

The processor 520 may obtain interval selection factors, and determine an interval selection indicator based on the interval selection factors. As described above, the interval selection factors may correspond to interval division factors and the interval selection indicator may correspond to an interval division indicator. That is, the interval selection factors may include a physiological characteristic, a physical characteristic, or an optical characteristic, such as an initial value of an optical property (e.g., scattering coefficient or effective attenuation coefficient), a height, a weight, a BMI, a body fat, or the like, and the interval selection indicator may be determined by a linear or nonlinear combination of the interval selection factors.

According to an embodiment, the processor 520 may obtain interval selection factors (particularly, an initial value of an optical property) via the optical sensor 510, obtain interval selection factors from an external device, or request the user to input interval selection factors and obtain interval selection factors by receiving an input in response to the request. In addition, the processor 520 may determine an interval selection indicator by linearly or nonlinearly combining the obtained interval selection factors. For example, the processor 520 may use Equation 1 shown elsewhere herein.

The processor 520 may select a blood concentration estimation model to be used in estimating blood concentration of an analyte from among the interval-specific blood concentration estimation models based on the determined interval selection indicator. According to an embodiment, the processor 520 may determine a blood concentration change interval of an analyte of interest based on the interval selection indicator, and may select a blood concentration estimation model that corresponds to the determined blood concentration change interval. For example, in the example illustrated in FIG. 3, when an initial value of an effective attenuation coefficient of an object is less than or equal to 0.15, the processor 520 may determine that the blood concentration change interval of the analyte of interest is the interval 1, and may select the blood concentration estimation model 310 which corresponds to the interval 1 as the model to be used in estimating blood concentration. Alternatively, when the initial value of the effective attenuation coefficient of the object is greater than 0.15, the processor 520 may determine that the blood concentration change interval of the object is the interval 2, and may select the blood concentration estimation model 320 which corresponds to the interval 2 as the model to be used in estimating blood concentration.

The processor 520 may change an optical property based on the optical signal detected by the optical sensor 510. In this case, the optical property may include a scattering coefficient, an effective attenuation coefficient, and the like.

According to an embodiment, the processor 520 may determine a scattering coefficient using Equation 2 shown below, and determine a change of the scattering coefficient based on the determined scattering coefficient and an initial value of the scattering coefficient.

$$\mu_s' = \frac{1}{3\mu_a}\left\{\frac{1}{\rho_2 - \rho_1}\ln\frac{\rho_1^2 R(\rho_1)}{\rho_2^2 R(\rho_2)}\right\}^2 \qquad \text{Equation (2)}$$

Here, $\mu_s'$ may denote a scattering coefficient, $\mu_a$ may denote an absorption coefficient, $\rho_1$ may denote a distance between a light source and a first photodetector, $\rho_2$ may denote a distance between the light source and a second photodetector, $R(\rho_1)$ may denote an intensity of an optical signal detected by the first photodetector, and $R(\rho_2)$ may denote an intensity of an optical signal detected by the second photodetector.

According to an embodiment, the processor 520 may determine an effective attenuation coefficient using Equation 3 shown below, and determine a change of the effective attenuation coefficient based on the determined effective attenuation coefficient and an initial value of the effective attenuation coefficient.

$$\ln\left(\rho^2 \frac{R(\rho)}{S_0}\right) = -\mu_{eff}\rho + \ln\left(\frac{3\mu_a}{2\pi\mu_{eff}}\right) \qquad \text{Equation (3)}$$

Here, $\rho$ may denote a distance between a light source and an arbitrary photodetector, $R(\rho)$ may denote an intensity of an optical signal detected by the arbitrary photodetector, $S_0$ may denote an intensity of light emitted from the light source, $\mu_{eff}$ may denote an effective attenuation coefficient, and $\mu_a$ may denote an absorption coefficient.

When the change of the optical property is determined, the processor 520 may estimate the blood concentration change or blood concentration of the analyte using the determined change of the optical property and the selected blood concentration estimation model.

Figure 6:
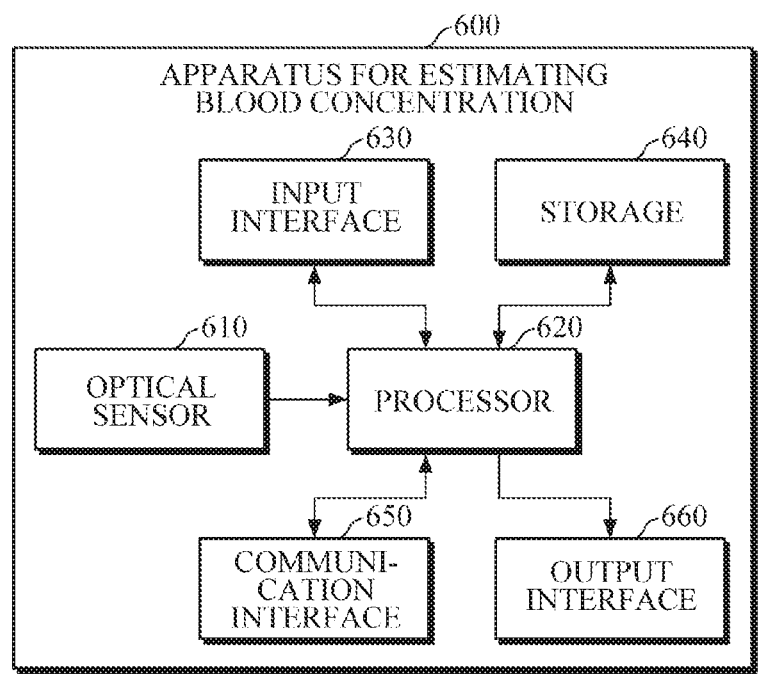
FIG. 6 is a block diagram illustrating an apparatus for estimating blood concentration according to an embodiment.

FIG. 6 is a block diagram illustrating an apparatus for estimating blood concentration according to an embodiment. The apparatus 600 for estimating blood concentration of FIG. 6 may be an apparatus configured to measure blood concentration of an analyte or a change of the blood concentration in a noninvasive manner using an optical signal, and may be mounted in an electronic device. The electronic device may include a mobile phone, a smartphone, a tablet computer, a notebook computer, a PDA, a PMP, a navigation system, an MP3 player, a digital camera, a wearable device, and the like. The wearable device may include a wrist watch type, a wrist band type, a ring type, a belt type, a necklace type, an ankle band type, a thigh band type, a forearm band type, and the like. However, the electronic device and the wearable device are not limited to the above-described examples.

Referring to FIG. 6, the apparatus 600 for estimating blood concentration may include an optical sensor 610, a processor 620, an input interface 630, a storage 640, a communication interface 650, and an output interface 660. Here, the optical sensor 610 and the processor 620 may be substantially similar as the optical sensor 510 and the processor 520 of FIG. 5, respectively, and thus detailed descriptions thereof might not be reiterated.

The input interface 630 may receive various operation signals based on a user input. According to an embodiment, the input interface 630 may include a key pad, a dome switch, a touch pad (e.g., a resistive touch page, a capacitive touch pad, etc.), a jog wheel, a jog switch, a hardware button, and the like. In particular, when a touch pad has a layered structure with a display, the structure may be referred to as a touch screen.

A program or commands for operations of the apparatus 600 for estimating blood concentration may be stored in the storage 640 and data input to and output from the apparatus 600 may be stored in the storage 640. In addition, a detected optical signal, an optical property and a change of the optical property which are determined based on the detected optical signal, interval-specific blood concentration estimation models, and a result of estimation of blood concentration of an analyte may be stored in the storage 640. The storage 640 may include at least one type of storage medium, such as a flash memory type, a hard disk type, a multimedia card micro type, a card type memory (e.g., secure digital (SD) or eXtreme digital (XD) memory), a random access memory (RAM), a static random access memory (SRAM), a read-only memory (ROM), an electrically-erasable programmable read-only memory (EEPROM), a programmable read-only memory(PROM), a magnetic memory, a magnetic disk, and an optical disk. In addition, the apparatus 600 for estimating blood concentration may communicate with an external storage medium, such as a web storage that performs the storage function of the storage 640 on the Internet.

The communication interface 650 may communicate with an external device. For example, the communicator 650 may transmit data input to, data stored in, and data processed by the apparatus 600 for estimating blood concentration to the external device or receive a variety of data for estimating blood concentration of an analyte from the external device.

In this case, the external device may be a medical device which uses the data input to, the data stored in, and the data processed by the apparatus 600 for estimating blood concentration, or a printer or a display device for outputting a result. In addition, the external device may include a digital television (TV), a desktop computer, a mobile phone, a smartphone, a tablet computer, a notebook computer, a PDA, a PMP, a navigation system, an MP3 player, a digital camera, a wearable device, and the like, but is not limited thereto.

The communication interface 650 may communicate with the external device using Bluetooth® communication, Bluetooth® low energy (BLE) communication, near field communication (NFC), wireless local access network (WLAN)

communication, ZigBee® communication, infrared data association (IrDA) communication, wireless fidelity (Wi-Fi) communication, ultra-wideband (UWB) communication, Ant+® communication, Wi-Fi direct (WFD) communication, radio frequency identification (RFID) communication, third generation (3G) communication, fourth generation (4G) communication, and fifth generation (5G) communication. However, these are merely examples and the types of communication are not limited thereto.

The output interface 660 may output the data input to, the data stored in, and the data processed by the apparatus 600 for estimating blood concentration. According to an embodiment, the output interface 660 may output the data input to, the data stored in, and the data processed by the apparatus 600 using at least one of an audible method, a visual method, and a tactile method. To this end, the outputter 660 may include a speaker, a display, a vibrator, and the like.

Figure 7:
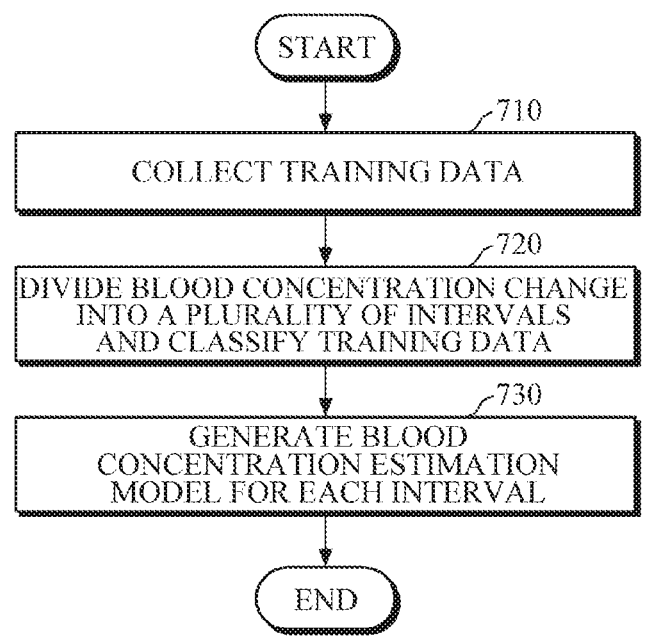
FIG. 7 is a flowchart illustrating a method of generating a blood concentration estimation model according to an embodiment.

FIG. 7 is a flowchart illustrating a method of generating a blood concentration estimation model according to an embodiment. The method shown in FIG. 7 may correspond to a method performed by the apparatus 110 of FIG. 1 to generate a model.

Referring to FIGS. 1 and 7, the apparatus 110 for generating a model may collect, as training data, optical property change data and blood concentration change data of an analyte that corresponds to the optical property change data, or collect, as training data, normalized optical property change data and a normalized blood concentration change data of the analyte that corresponds to the normalized optical property change data (operation 710). In this case, the normalized optical property change data may be data in which the optical property change data is normalized to an initial value of an optical property, and the normalized blood concentration change data may be data in which the blood concentration change data is normalized to an initial blood concentration value.

The apparatus 110 for generating a model may divide a blood concentration change or a normalized blood concentration change of an analyte into a plurality of intervals according to an interval division indicator and classify the collected training data for each interval (operation 720). As described above, the interval division indicator may be formed by a linear or nonlinear combination of interval division factors including an initial value of an optical property (e.g., scattering coefficient or effective attenuation coefficient), a height, a weight, a BMI, a body fat, and the like. For example, the interval division indicator may be represented as a linear combination of interval division factors as shown in Equation 1 elsewhere herein.

The apparatus 110 for generating a model may generate a blood concentration estimation model for each interval by using the training data classified for each interval (operation 730). According to an embodiment, the apparatus 110 may generate the blood concentration estimation for each interval using a regression analysis technique or a machine learning technique.

Figure 8:
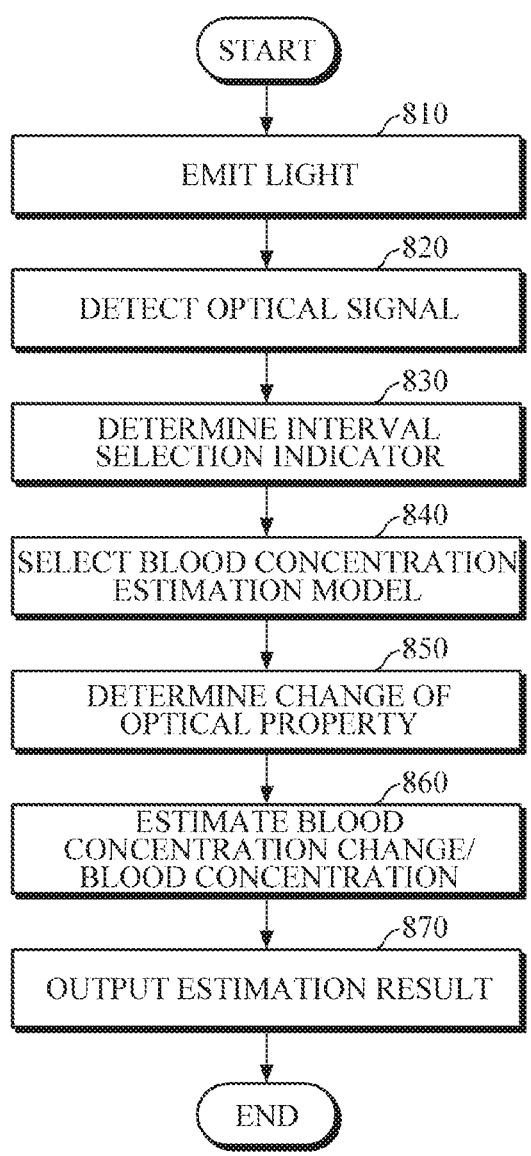
FIG. 8 is a flowchart illustrating a method of estimating blood concentration of an analyte according to an embodiment.

FIG. 8 is a flowchart illustrating a method of estimating blood concentration of an analyte according to an embodiment. The method shown in FIG. 8 may correspond to a method performed by the apparatus 120 of FIG. 1 to estimate blood concentration.

Referring to FIGS. 1 and 8, the apparatus 120 for estimating blood concentration may emit light towards a skin of a user (operation 810), and detect an optical signal reflected by the skin (operation 820).

The apparatus 120 for estimating blood concentration may obtain an interval selection factor, and determine an interval selection indicator based on the interval selection factor (operation 830). As described above, the interval selection factor may correspond to an interval division factor, and the interval selection indicator may correspond to an interval division indicator. That is, the interval selection factor may include a physiological characteristic, a physical characteristic, or an optical characteristic, such as an initial value of an optical property (e.g., scattering coefficient or effective attenuation coefficient), a height, a weight, a BMI, a body fat, or the like, and the interval selection indicator may be determined by a linear or nonlinear combination of the interval selection factors.

According to an embodiment, the apparatus 120 for estimating blood concentration may obtain the interval selection factor via the optical sensor, obtain the interval selection factor from an external device, or request the user to input the interval selection factor and obtain the interval selection factor by receiving an input in response to the request. In addition, the apparatus 120 for estimating blood concentration may determine an interval selection indicator by linearly or nonlinearly combining the obtained interval selection factors. For example, the apparatus 120 for estimating blood concentration may determine the interval selection indicator using Equation 1 as shown elsewhere herein.

The apparatus 120 for estimating blood concentration may select a blood concentration estimation model to be used in estimating blood concentration of an analyte from among the interval-specific blood concentration estimation models based on the determined interval selection indicator (operation 840). For example, the apparatus 120 for estimating blood concentration may determine a blood concentration change interval of the analyte of interest based on the interval selection indicator, and select a blood concentration estimation model that corresponds to the determined blood concentration change interval.

The apparatus 120 for estimating blood concentration may determine a change of an optical property based on the detected optical signal (operation 850). For example, the apparatus 120 for estimating blood concentration may determine an optical property using Equation 2 or Equation 3 shown elsewhere herein, and determine a change of the optical property based on an initial value of the optical property.

Based on determining the change of the optical property, the apparatus 120 for estimating blood concentration may estimate blood concentration change or blood concentration of the analyte using the determined change of the optical property and the blood concentration estimation model (operation 860), and provide, for output via an output interface, the estimation result (operation 870).

Figure 9:
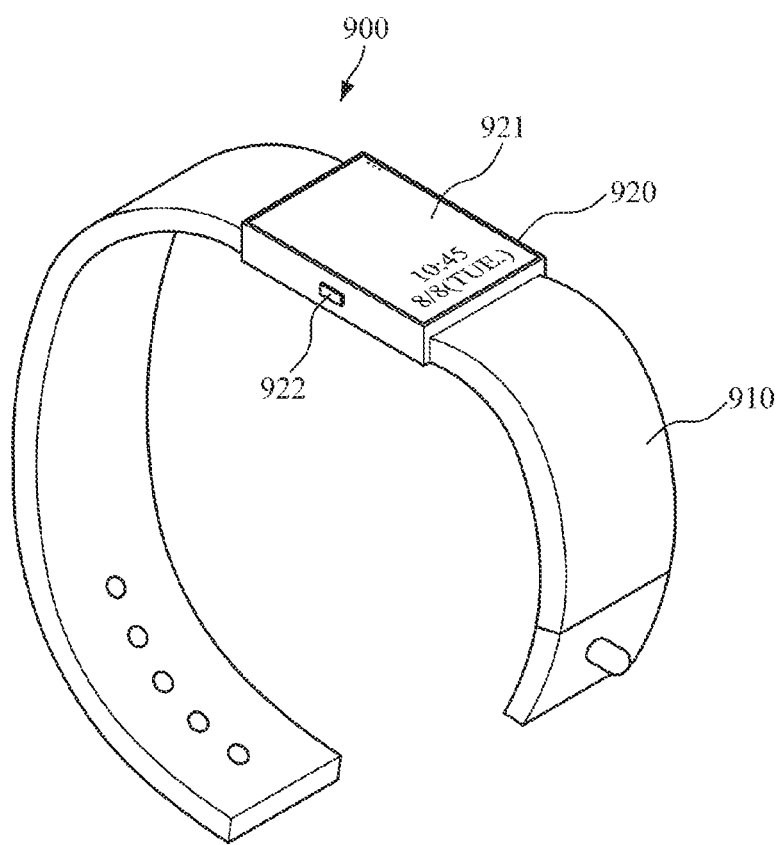
FIG. 9 is a diagram illustrating a wrist type wearable device according to an embodiment.

FIG. 9 is a diagram illustrating a wrist type wearable device.

Referring to FIG. 9, the wrist type wearable device 900 may include a strap 910 and a main body 920.

The strap 910 may be may be separated into two members that are connected to each end of the main body, and configured to be coupled to each other, or may be integrally formed in the form of a smart band. The strap 910 may be formed of a flexible material to wrap around a user's wrist such that the main body 920 can be placed on the user's wrist.

The main body 920 may include the above-described apparatuses 110 or 200 for generating a model and the apparatuses 120, 500, or 600 for estimating blood concentration mounted therein. In addition, a battery may be embedded in the main body 920 to supply power to the wrist type wearable device 900, the apparatuses 110 or 200 for generating a model, and/or the apparatuses 120, 500, or 600 for estimating blood concentration.

An optical sensor may be mounted in a lower part of the main body 920 such that the optical sensor is exposed to the user's wrist. Accordingly, when the user wears the wrist type wearable device 900, the optical sensor is naturally brought into contact with the skin of the user.

The wrist wearable device 900 may further include a display 921 and an input interface 922 which are mounted in the main body 920. The display 921 may display data processed by the wrist type wearable device 900, the apparatuses 110 or 200 for generating a model, and/or the apparatuses 120, 500, or 600 for estimating blood concentration and the processing result data. The input interface 922 may receive various operation signals from the user.

The current embodiments can be implemented as computer readable code stored in a non-transitory computer-readable medium. Code and code segments constituting the computer program can be inferred by a skilled computer programmer in the art. The computer-readable medium includes all types of recording media in which computer-readable data are stored. Examples of the computer-readable medium may include a ROM, a RAM, a CD-ROM, a magnetic tape, a floppy disk, and an optical data storage. Further, the computer-readable medium may be implemented in the form of a carrier wave such as Internet transmission. In addition, the computer-readable medium may be distributed to computer systems via a network, in which computer readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating blood concentration, comprising:
   an optical sensor configured to emit light towards a skin surface of a user, and detect an optical signal reflected by the skin surface of the user; and
   a processor configured to:
      determine an interval selection indicator based on an initial value of an effective attenuation coefficient of the optical signal;
      select an interval-specific blood concentration estimation model, from among a plurality of interval-specific blood concentration estimation models in which ratios between the effective attenuation coefficient and a blood concentration change interval are different from each other, based on the interval selection indicator; and
      estimate a blood concentration change or a blood concentration of an analyte using the selected interval-specific blood concentration estimation model and the detected optical signal.

2. The apparatus of claim 1, wherein the processor is further configured to:
   obtain a plurality of interval selection factors; and
   determine the interval selection indicator by linearly or nonlinearly combining the obtained plurality of interval selection factors.

3. The apparatus of claim 2, wherein the initial value of the effective attenuation coefficient is one of the plurality of interval selection factors, and wherein the plurality of interval selection factors also includes at least one of an initial value of an optical property that is different from the effective attenuation coefficient, a height, a weight, a body mass index (BMI), and a body fat.

4. The apparatus of claim 1, wherein the processor is further configured to:
   determine a change of an optical property based on the detected optical signal; and
   estimate the blood concentration change or blood concentration of the analyte using the determined change of the optical property and the selected interval-specific blood concentration estimation model.

5. The apparatus of claim 4, wherein the optical property is a scattering coefficient or the effective attenuation coefficient.

6. The apparatus of claim 1, wherein the analyte includes at least one of glucose, triglyceride, cholesterol, protein, lactate, ethanol, uric acid, and ascorbic acid.

7. The apparatus of claim 1, wherein the plurality of interval-specific blood concentration estimation models are generated based on training data classified based on an interval division indicator that corresponds to the interval selection indicator.

8. The apparatus of claim 1, further comprising an output interface configured to output the estimated blood concentration change or the blood concentration of the analyte.

9. A method of estimating blood concentration, comprising:
   emitting light towards a skin surface of a user;
   detecting an optical signal reflected by the skin surface of the user;
   determining an interval selection indicator based on an initial value of an effective attenuation coefficient of the optical signal;
   selecting an interval-specific blood concentration estimation model, from among a plurality of interval-specific blood concentration estimation models in which ratios between the effective attenuation coefficient and a blood concentration change interval are different from each other, based on the interval selection indicator; and
   estimating a blood concentration change or a blood concentration of an analyte using the selected interval-specific blood concentration estimation model and the detected optical signal.

10. The method of claim 9, further comprising:
    obtaining a plurality of interval selection factors; and
    determining the interval selection indicator by linearly or nonlinearly combining the obtained plurality of interval selection factors.

11. The method of claim 10, wherein the initial value of the effective attenuation coefficient is one of the plurality of interval selection factors, and wherein the plurality of interval selection factors also includes at least one of an initial value of an optical property that is different from the effective attenuation coefficient, a height, a weight, a body mass index (BMI), and a body fat.

12. The method of claim 9, wherein the estimating of the blood concentration change or the blood concentration of the analyte comprises:
    determining a change of an optical property based on the detected optical signal; and
    estimating the blood concentration change or the blood concentration of the analyte using the determined change of the optical property and the selected interval-specific blood concentration estimation model.

13. The method of claim 12, wherein the optical property is a scattering coefficient or the effective attenuation coefficient.

14. The method of claim 9, wherein the analyte includes at least one of glucose, triglyceride, cholesterol, protein, lactate, ethanol, uric acid, and ascorbic acid.

15. The method of claim 9, wherein the plurality of interval-specific blood concentration estimation models are generated based on training data classified according to an interval division indicator that corresponds to the interval selection indicator.

16. The method of claim 9, further comprising:
outputting the estimated blood concentration change or the blood concentration of the analyte.

17. A wearable device for measuring a triglyceride level of a user, comprising:

an optical sensor configured to emit light towards a skin surface of the user, and detect an optical signal reflected by the skin surface of the user; and a processor configured to:
determine an interval selection indicator based on an initial value of an effective attenuation coefficient of the optical signal;
identify a triglyceride level estimation model, from among a plurality of triglyceride level estimation models in which ratios between the effective attenuation coefficient and a blood concentration change interval are different from each other, based on the interval selection indicator; and
estimate the triglyceride level of the user based on the identified triglyceride estimation model and the detected optical signal.

* * * * *